United States Patent
Quinlan et al.

(10) Patent No.: US 7,354,614 B2
(45) Date of Patent: Apr. 8, 2008

(54) DIAGNOSTIC DEVICE

(75) Inventors: Kevin Michael Quinlan, Hampshire (GB); John Amey, Hampshire (GB); Emma Whitworth, South Wales (GB)

(73) Assignees: Porvair Filtration Group Ltd., Fareham, Hampshire (GB); British Biocell International Limited, Cardiff (GB)

( * ) Notice: Subject to any disclaimer, the term of this patent is extended or adjusted under 35 U.S.C. 154(b) by 0 days.

(21) Appl. No.: 11/424,669

(22) Filed: Jun. 16, 2006

(65) Prior Publication Data
US 2007/0031978 A1 Feb. 8, 2007

(30) Foreign Application Priority Data
Jun. 16, 2005 (GB) .................. 0512323.7

(51) Int. Cl.
*G01N 33/53* (2006.01)
(52) U.S. Cl. .................. 426/514; 436/514; 436/518; 436/524; 436/538; 436/535; 436/810; 436/807; 435/7.1; 435/7.2; 435/7.8; 435/7.92; 435/7.94; 435/287.1; 435/174; 435/970; 435/971
(58) Field of Classification Search ............... 436/514, 436/518, 524, 538, 535, 810, 807; 435/7.1, 435/7.2, 7.8, 7.92, 7.94, 287.2, 174, 970, 435/971, 287.1; 422/58–61
See application file for complete search history.

(56) References Cited

U.S. PATENT DOCUMENTS

| | | | |
|---|---|---|---|
| 4,693,834 A * | 9/1987 | Hossom | 210/767 |
| 5,078,968 A * | 1/1992 | Nason | 422/58 |
| 5,547,833 A | 8/1996 | Dorval et al. | |
| 5,763,262 A | 6/1998 | Wong et al. | |
| 5,935,864 A * | 8/1999 | Schramm et al. | 436/174 |
| 6,130,097 A | 10/2000 | Polzius et al. | |
| 6,475,804 B1* | 11/2002 | Lohse | 436/506 |
| 6,893,880 B2* | 5/2005 | Carpenter | 436/514 |

FOREIGN PATENT DOCUMENTS

| | | |
|---|---|---|
| CA | 2216214 | 5/1999 |
| EP | 0401913 | 12/1990 |
| EP | 1043588 | 11/2000 |
| GB | 2239314 | 6/1991 |
| WO | 88/08534 | * 11/1988 |
| WO | 97/23781 | 7/1997 |
| WO | 98/13519 | 4/1998 |
| WO | 99/14598 | 3/1999 |

OTHER PUBLICATIONS

UK Search Report.

* cited by examiner

*Primary Examiner*—Bao-Thuy L. Nguyen
(74) *Attorney, Agent, or Firm*—Renner, Otto, Boisselle & Sklar, LLP.

(57) ABSTRACT

A diagnostic device 1 for performing an immunochromatographic analysis of a sample is disclosed. The diagnostic device 1 comprises a porous substrate 10 for performing the analysis and a pre-filter 30 to remove solid components, such as solubilised faeces or samples containing suspended organic material to prevent blocking of the porous substrate or coloured particles so that the test result is more clearly visible. The diagnostic device may include a container into which a sample may be provided, with the interior of the container being sealably connectable to the diagnostic section of the device. The porous section may be encapsulated within a housing.

3 Claims, 6 Drawing Sheets

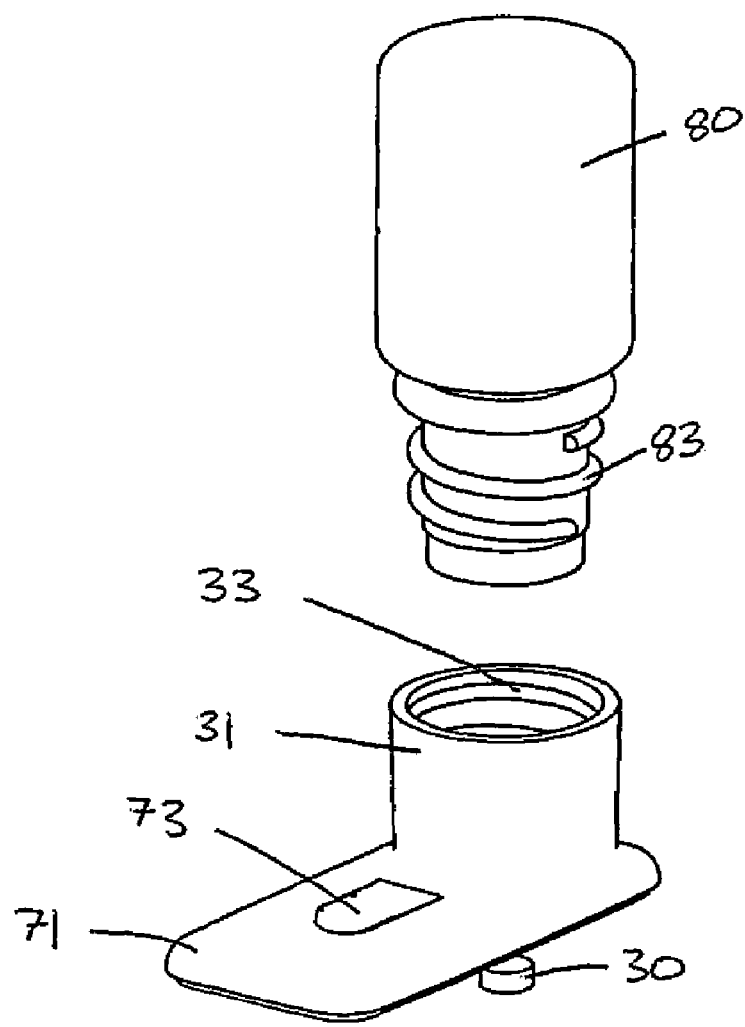
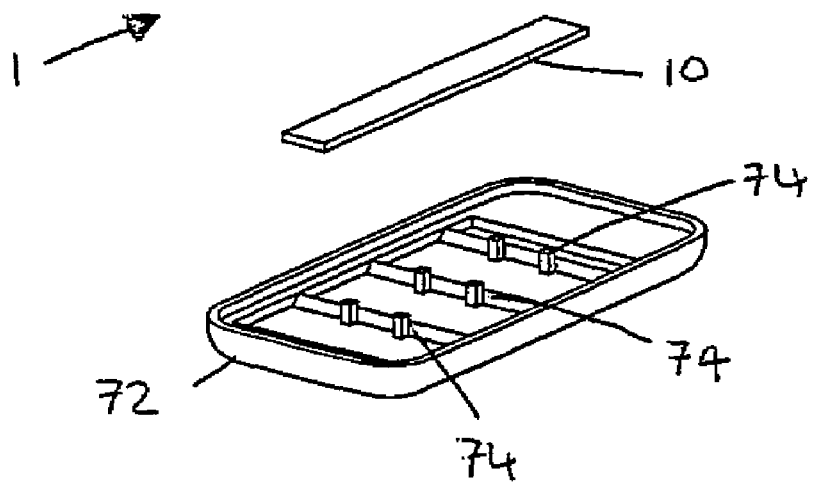
Figure 5

DIAGNOSTIC DEVICE

The present invention relates to a diagnostic device and a method of performing an analysis. Embodiments of the present invention disclose a diagnostic device that enables direct immunochromatographic analysis of a sample with a high solids content.

Immunochromatographic assays, also called lateral flow tests or strip tests have been used for several decades. They are an extension of the technology used in latex agglutination tests. Essentially any liquid that can be bound to a visually detectable solid support can be tested for qualitatively. Typical tests involve providing a sample to be tested for a particular ligand at one end of a strip formed from a porous substrate. The sample moves along the strip by capillary action reaching a portion of the strip containing a visually detectable solid support such as a colloidal gold/antibody conjugate which is arranged to bind to the ligand being tested for. If the ligand being tested for is present, it binds to the visually detectable solid support and a second antibody, immobilised as a line in the strip, then captures the complex. If the test is positive, a coloured line develops. Results can usually be read in 10 to 20 minutes. Strip tests are suitable for home testing because of their user-friendly format and the short time required to obtain a test result. Some of the more common strip tests currently on the market are tests for pregnancy, strep throat and chlamydia.

However, there are a number of problems associated with conventional strip tests. One problem is that it is difficult to use strip tests with samples that contain solid components, such as solubilised faeces or samples containing suspended organic material, as the solid components tend to block the porous substrate of the strip preventing the sample from flowing along the strip. A further problem arises when trying to use a strip test with a non-clear sample such as blood or urine as the colour from the sample may obscure the coloured line indicating whether or not the test is positive so that the results cannot be clearly determined.

The present invention seeks to alleviate or overcome at least one of these problems.

According to a first aspect of the present invention there is provided a diagnostic device for performing an immunochromatographic analysis of a sample, the device comprising:

a porous substrate for a visually detectable indicator arranged to bind to a ligand or other material being tested for and a filter arranged to act on a sample being tested before at least a portion of the sample encounters the porous substrate.

The filter enables the diagnostic device to work particularly well with samples that contain solid components as the filter collects the solid components enabling the fluid portion to progress to the porous substrate to be tested, without blocking it. Similarly, the diagnostic device works particularly well with non-clear samples such as blood or urine as the filter removes at least some of the coloured particles providing a much clearer test result.

The filter is preferably hydrophilic or the device has a hydrophilic portion to draw the sample through towards the porous substrate. This provides a more uniform sample flow and minimises the need for mechanical input.

The device may have a container into which a sample may be provided and the container may be sealably connectable to the diagnostic device. The provision of a sample into a container may be more convenient than providing a sample onto the diagnostic device, and as the container is sealably connectable to the diagnostic device, there is a much reduced risk of contamination or soiling during analysis, handling and disposal. The provision of a container which is sealably connectable to the diagnostic device reduces the components to a single assembly minimising user confusion. Furthermore, the use of a container into which sample may be provided enables the sample to be pre-treated, such as by being mixed with appropriate reagants or a buffer or shaken.

The entire diagnostic device may be encapsulated within a housing to prevent contact with or exposure to the sample.

The container for holding the sample may attach and seal directly to the diagnostic device which preferably houses the filter in intimate contact with the porous substrate.

The device may include a dosing portion arranged to receive up to a predetermined maximum volume of a sample from the filter. The dosing portion may be arranged to be moved out of contact with the filter and into contact with the porous substrate.

According to a second aspect of the present invention there is provided a method of performing an analysis on a sample, the method comprising:

filtering a sample to be tested and providing the filtered sample to a porous substrate for a visually detectable indicator to bind to a ligand or other material being tested for, if present in the sample.

Embodiments of the present invention will now be described, by way of example only, with reference to the accompanying drawings, in which:

FIG. 5 shows an exploded perspective view of a further diagnostic device with an associated container;

Figure 1:
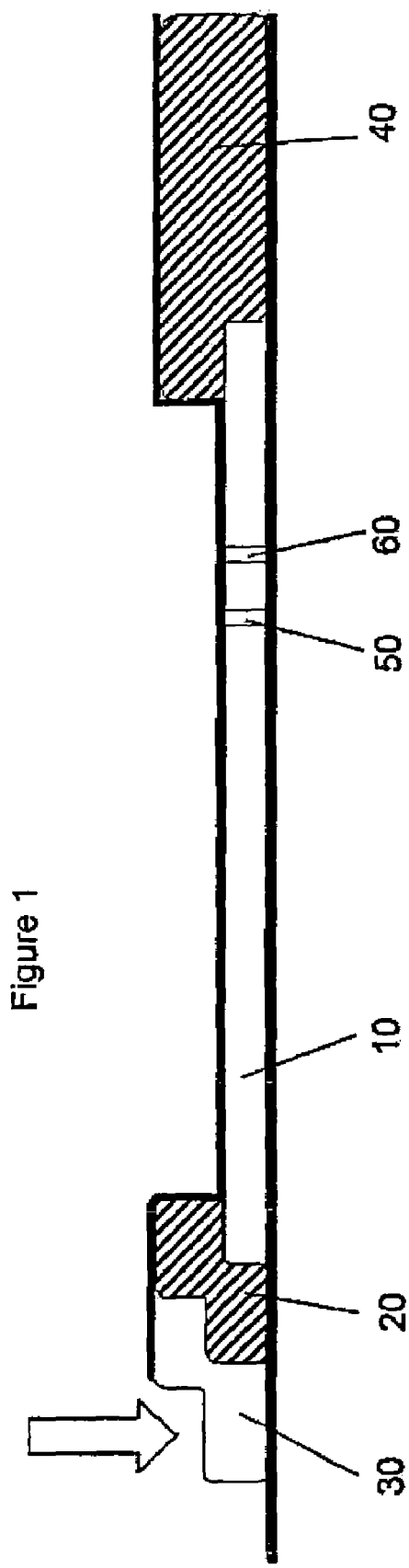
FIG. 1 shows a schematic side view of a diagnostic device comprising a porous substrate with a filter.

As shown in FIG. 1, a diagnostic device 1 for performing an immunochromatographic analysis on a sample comprises a porous substrate 10, in this example made from nitrocellulose, with a visually detectable support 20, in this example a colloidal gold/antibody conjugate, provided in the porous substrate 10 to be bound to a ligand or other material being tested for. A filter 30 is arranged to pre-filter a sample provided thereon as indicated by the arrow. In this example the filter 30 is a non-woven pre-filter preferably made from a plastics material. As explained, the filter 30 collects solid components and/or at least some coloured particles from the sample such that the porous substrate 10 is not blocked and contains less coloured sample and so produces a more easily read result.

In use, after being provided on the filter 30, solid components and/or coloured particles are collected in the filter 30 whilst fluid progresses along to the porous substrate 10 by capillary action, drawn by the absorbent cellulose 40 at the opposite end of the porous substrate 10. The fluid component of the sample reaches the visually detectable support 20. If the ligand or other material being tested for is present in the fluid component of the sample, the visually detectable support 20 binds to it. The fluid sample then continues to pass along the porous substrate 10 until it reaches a line 50, in this example containing a second antibody, to capture the sample. If the sample contains the visually detectable support 20 as a complex, a coloured line develops indicating a positive test result. If the ligand or other material being tested for is not present, it would not have become bound to the detectable support 20 and a coloured line would not have developed at point 50. If desired, a second line 60 may be provided to indicate that the fluid sample has progressed as far as line 50 to confirm that the test has been satisfactorily performed, as is well known in the art.

The filter 30 is preferably hydrophilic to make the sample flow more uniformly and to minimise the need for mechanical input.

Figure 2:
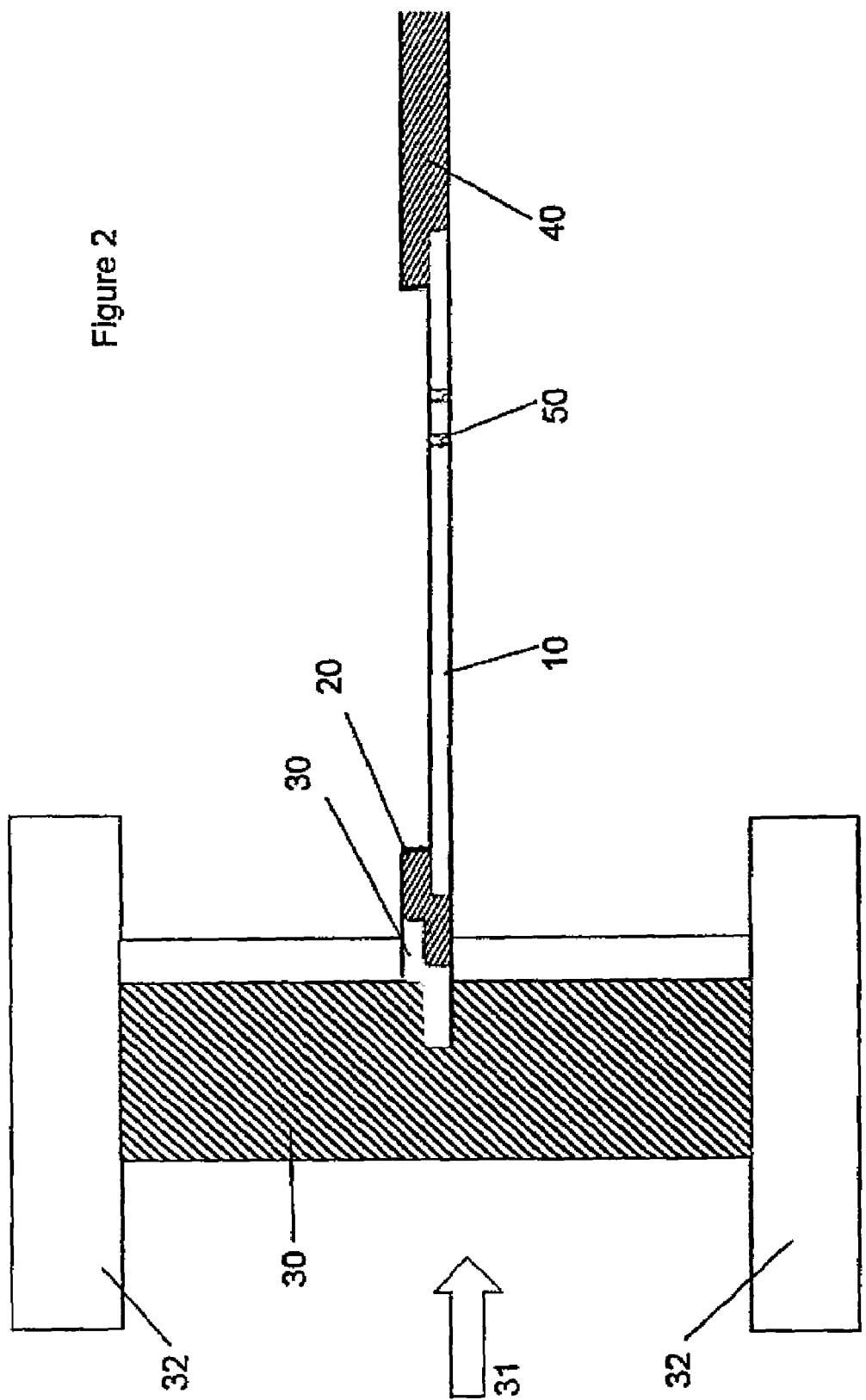
FIG. 2 shows a schematic cross-sectional side view of another diagnostic device.

FIG. 2 shows a schematic cross-sectional side view of another embodiment of the present invention. In this embodiment the filter 30 extends into a receptacle 31 arranged to receive a sample being tested. The receptacle 31 provides for more convenient provision of a sample onto the filter 30 as the receptacle 31 has sidewalls 32 to contain a sample therein.

Figure 3:
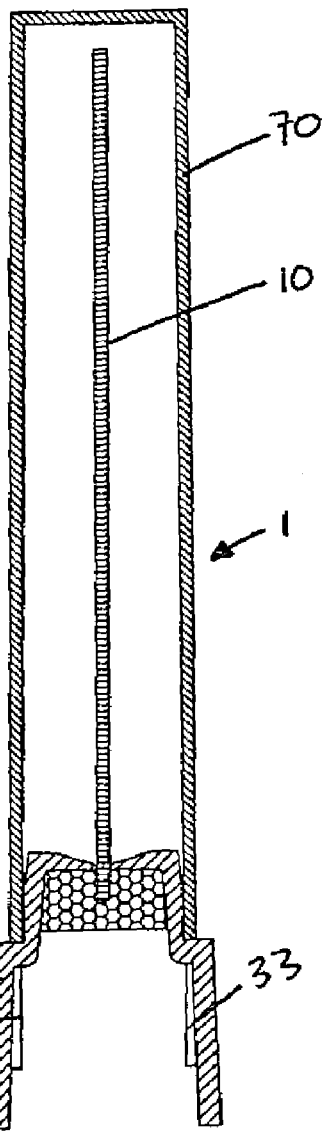
FIG. 3 shows a schematic cross-sectional side view of an encapsulated diagnostic device.
Figure 4:
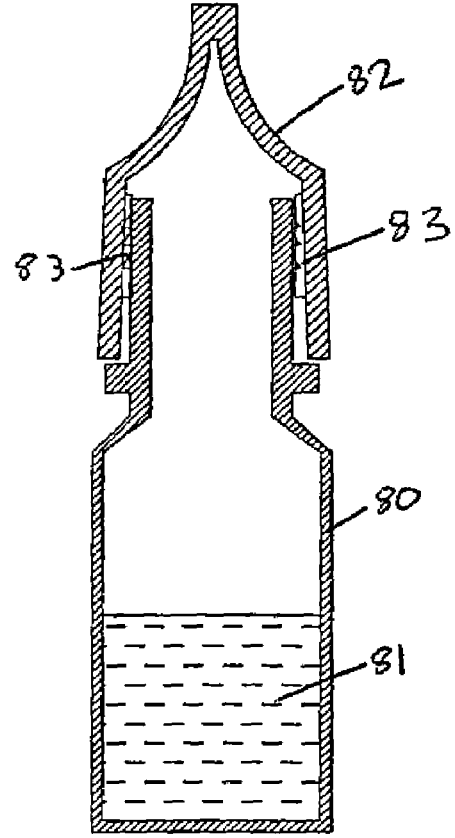
FIG. 4 shows a container to be used with the diagnostic device shown in FIG. 3.

FIG. 3 shows a schematic cross-sectional side view of another embodiment of the present invention. In this example the porous substrate 10 is encapsulated within a sheath 70 with at least one transparent portion to view the result to prevent contact with or exposure to the sample whilst on the porous substrate 10. The filter 30 is provided in this example within a receptacle 31 with means 33 for attachment to a sample preparation container 80 as shown in FIG. 4 in which a sample 81 may be provided. The sample 81 may have been mixed with suitable reagants or a buffer and shaken. The container 80 has a lid 82 to prevent contact with or exposure to the sample 81. Use of a separate container 80 enables a sample to be collected separately, for example by a person being tested, and then sealed with the lid 82 and taken to be tested with the diagnostic device. The container 80 has means 83 for attachment to the corresponding attachment means 33 of the diagnostic device shown in FIG. 3. The attachment means 33, 83 may be screw threads, push-fit attachments or any suitable attachment means. The attachment means 33, 83 provide a sealable connection between the container 80 and the diagnostic device 1 providing a much reduced risk of contamination or soiling during analysis, handling and disposal. The provision of two components (the device 1 and container 80) which are sealably connectable minimises user confusion and error.

The diagnostic device 1 and container 80 shown in FIGS. 3 and 4 are arranged to be attached together to form an in-line device. However, any suitable relative orientation of the diagnostic device 1 and container 80 may be provided, such as the off-set arrangement shown in the exploded perspective view of FIG. 5.

As shown in FIG. 5, the container 80 is sealably connectable to the receptable 31 of the diagnostic device 1 using threads 83 on the container 80 and corresponding threads 33 in the receptacle 31. The diagnostic device 1 encapsulates the porous substrate 10 with upper 71 and lower 72 portions of a sheath 70. A transparent portion 73 is provided in the upper portion 71 of the sheath so that the result of the test on the porous substrate 10 may be viewed. The filter 30 is housed in the diagnostic device 1 such that it may be provided in intimate contact adjacent to the porous substrate 10 to pre-filter a sample from the container 80. The lower portion 72 of the sheath includes mounting supports 74 for the porous substrate 10 to keep it in a stable position within the diagnostic device 1.

Figure 6:
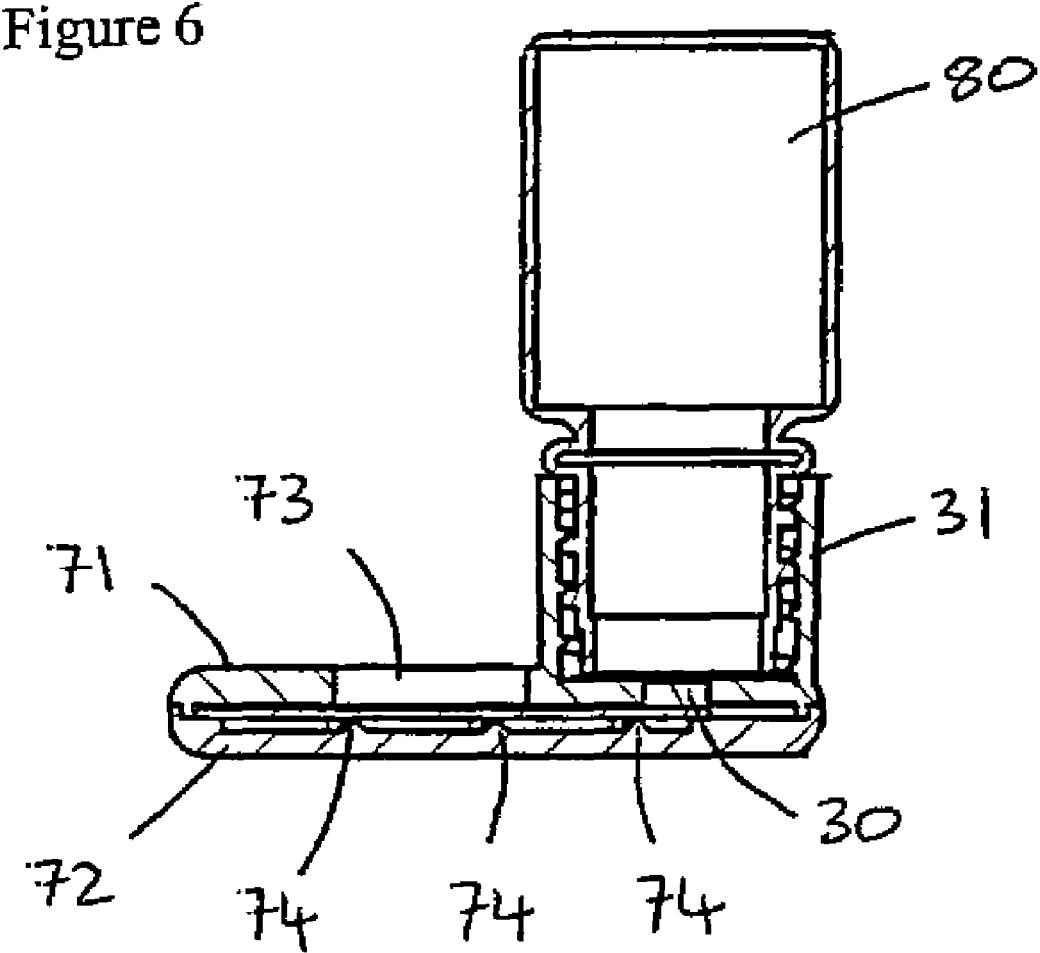
FIG. 6 shows a cross-sectional side view of the diagnostic device of FIG. 5 when assembled and FIG. 7 shows an arrangement for providing a stoichometric volume of a sample.

FIG. 6 shows a cross-sectional side view of the diagnostic device of FIG. 5 when assembled. As can be seen, the container 80 holding the sample attaches and seals directly to the main body of the diagnostic device 1 which houses the filter 30 in intimate contact with the porous substrate 10 being used as an immunochromatographic analysis strip.

Figure 7:
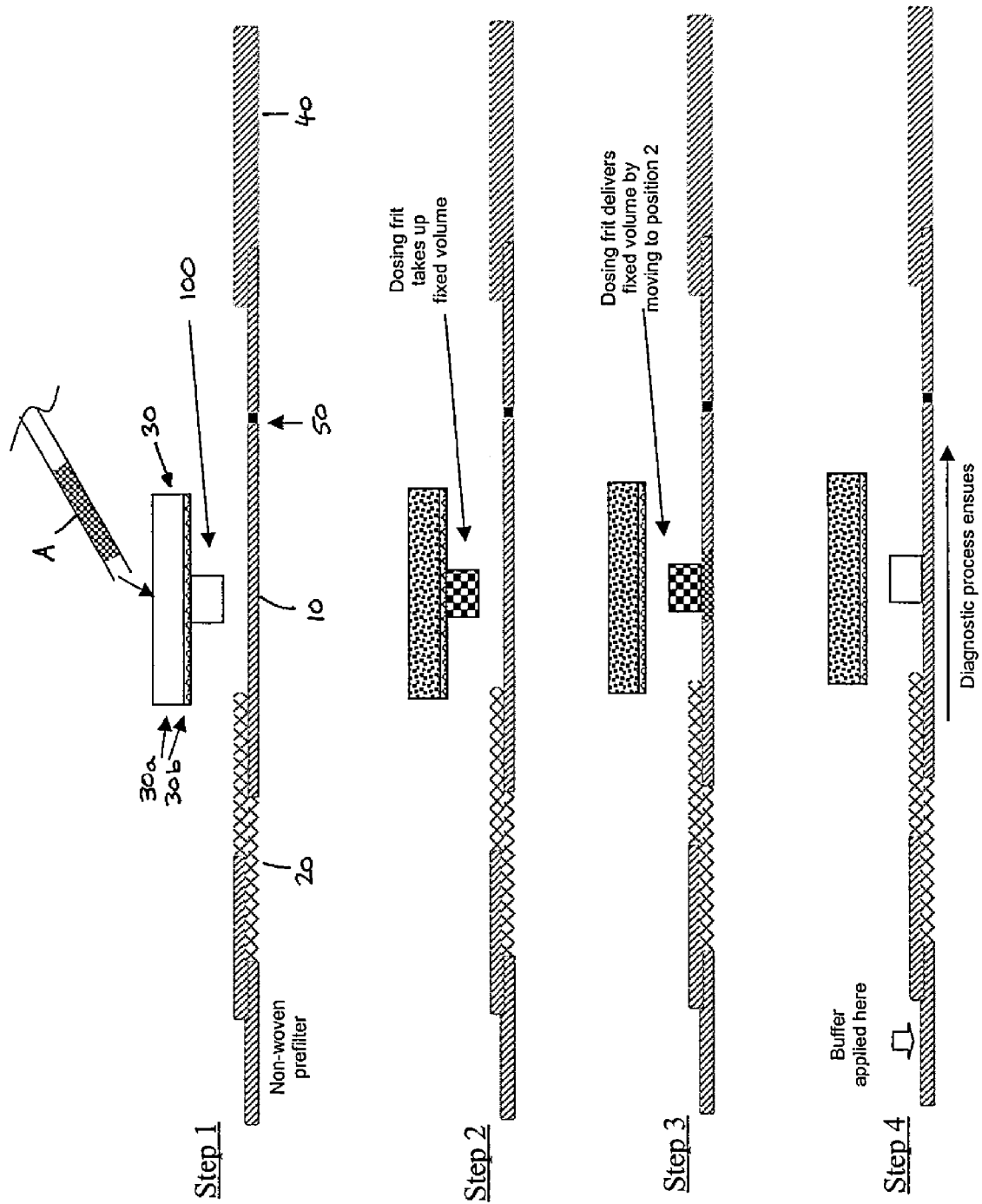

FIG. 7 shows an arrangement for providing a stoichiometric volume of a sample to a porous substrate 10. It is desirable for the porous substrate 10 not to be provided with an excessive volume of a sample as this could flood the substrate and impair the results. For example, for a typical diagnostic device, it is desirable not to exceed 10 μ of a sample such as blood.

The arrangement shown in FIG. 7 includes a dosing portion 100 arranged to receive up to a predetermined maximum volume of a sample from a filter 30. The dosing portion 100 may be a frit of porous material. In the example shown in FIG. 7 the filter 30 is composed of two sample filter layers 30a, 30b.

In step 1 of FIG. 7, the dosing portion 100 is shown in a first position in contact with the filter 30 but not in contact with the porous substrate 10. A sample from a suitable dispensing device A is then applied to the filter 30.

In step 2 of FIG. 7, the sample is seen to be absorbed into the filter 30 and dosing portion 100. The dosing portion 100 is arranged to receive up to a predetermined maximum volume of a sample from the filter 30, for example by being a predetermined size and having a predetermined porosity. The predetermined volume received by the dosing portion 100 is arranged to be suitable for the particular test being performed by the diagnostic device.

In step 3 of FIG. 7, the dosing portion 100 with a predetermined volume of a sample is moved out of contact with the filter 30 and into contact with the porous substrate 10. The movement of the dosing portion may be achieved by any suitable means such as a suitable actuator on the diagnostic device.

In step 4 of FIG. 7, as the dosing portion 100 is now in contact with the porous substrate 10, the predetermined volume of sample from the dosing portion 100 is drawn into the porous substrate 10 so that the diagnosis may be performed. In this example a buffer may also be applied to the diagnostic device.

As the filter 30 is never in contact with porous substrate 10 in the example of FIG. 7, buffer and conjugate cannot be sucked up from the porous substrate into the sample delivery device A.

The components of the diagnostic device may be made from any suitable materials such as combustible materials to enable disposal by incineration.

Many variations may be made to the examples described above. For example, the filter may be formed integrally with the porous strip or attached to it. The diagnostic device may for example be used with any immunochromatographic assay, lateral flow test or strip test.

The invention claimed is:

1. A diagnostic system for performing an immunochromatographic analysis of a sample, the system comprising:
   a filter operable to receive a sample to be tested,
   a dosing portion that contacts the filter to receive a predetermined volume of a sample from the filter, and
   a porous substrate having a visually detectable indicator arranged to bind to a ligand or other material being tested for in the sample,
   wherein,
   the system is configured so that the filter acts on the sample before a predetermined volume of the sample enters the dosing portion, and the dosing portion is configured to come into contact with the porous substrate to deliver the predetermined volume of the sample to the porous substrate.

2. The diagnostic device according to claim 1, wherein the filter is hydrophilic.

3. The diagnostic system according to claim 1, wherein the dosing portion is moved out of contact with the filter when the dosing portion is in contact with the porous substrate.

* * * * *